US009116138B2

(12) United States Patent
Okada et al.

(10) Patent No.: US 9,116,138 B2
(45) Date of Patent: Aug. 25, 2015

(54) EXHAUST GAS ANALYSIS SYSTEM AND PROGRAM FOR THIS SYSTEM

(71) Applicant: HORIBA, Ltd., Kyoto (JP)

(72) Inventors: Kaoru Okada, Kyoto (JP); Masayuki Hayata, Kyoto (JP); Toru Yamazaki, Kyoto (JP); Katsumi Uratani, Kyoto (JP)

(73) Assignee: HORIBA, Ltd., Kyoto (JP)

( * ) Notice: Subject to any disclaimer, the term of this patent is extended or adjusted under 35 U.S.C. 154(b) by 42 days.

(21) Appl. No.: 13/670,492

(22) Filed: Nov. 7, 2012

(65) Prior Publication Data
US 2013/0118244 A1  May 16, 2013

(30) Foreign Application Priority Data

Nov. 10, 2011 (JP) ................................. 2011-246280

(51) Int. Cl.
| G01N 33/497 | (2006.01) |
| G01N 33/00 | (2006.01) |
| G01N 1/22 | (2006.01) |
| G01N 35/10 | (2006.01) |

(52) U.S. Cl.
CPC .......... *G01N 33/0063* (2013.01); *G01N 1/2252* (2013.01); *G01N 35/1004* (2013.01)

(58) Field of Classification Search
CPC ....... Y02T 10/47; F01N 11/00; F01N 11/002; F02M 25/0702; G01M 15/102; B60W 10/06; C04B 35/62272; G01N 1/2252; G01N 2001/2264; B01D 46/46
USPC ............... 73/114.71, 114.69, 114.74, 114.76, 73/23.2
See application file for complete search history.

(56) References Cited

U.S. PATENT DOCUMENTS

| 3,917,454 A | * | 11/1975 | Clark ......................... 73/863.11 |
| 3,998,095 A | * | 12/1976 | Tinkham et al. ........... 73/114.71 |
| 4,315,243 A | * | 2/1982 | Calvert, Sr. ................... 340/449 |

(Continued)

FOREIGN PATENT DOCUMENTS

| CN | 1517522 A | 8/2004 |
| CN | 101091038 A | 12/2007 |

(Continued)

OTHER PUBLICATIONS

Office Action dated May 6, 2015 issued for Chinese patent application No. 201210441594.0, 11 pgs.

*Primary Examiner* — Peter Macchiarolo
*Assistant Examiner* — Mohammed Keramet-Amircola
(74) *Attorney, Agent, or Firm* — Brooks Kushman P.C.

(57) ABSTRACT

The exhaust gas analysis system urges a user to conduct a purge in an exhaust gas flow line by not only informing the user of the timing that the purge is necessary from the exhaust gas analysis system but also making it easy for the user to recognize the information. The exhaust gas analysis system comprises an exhaust gas flow line (L) where an exhaust gas flows, a measurement device 2, 3 that is arranged in the exhaust gas flow line (L) and that includes a pollutant component meter to measure a pollutant component to be a cause of pollutant of the exhaust gas flow line, and a display control device 5 that compares a measurement signal value obtained by the pollutant component meter or its arithmetic value with a predetermined pollutant component tolerance and that displays a warning window on a display 21 in case that the measurement signal value or the arithmetic value exceeds the predetermined pollutant component tolerance.

10 Claims, 9 Drawing Sheets

(56) References Cited

U.S. PATENT DOCUMENTS

| | | |
|---|---|---|
| 5,410,907 A | 5/1995 | Strom et al. |
| 5,907,109 A | 5/1999 | Tedeschi |
| 5,916,294 A * | 6/1999 | Naber et al. ............ 701/109 |
| 5,993,743 A | 11/1999 | Nordman et al. |
| 7,891,177 B2 * | 2/2011 | Ammineni et al. ........ 60/297 |
| 8,489,270 B2 * | 7/2013 | Wehmeier et al. ........ 701/29.7 |
| 2008/0264045 A1 | 10/2008 | Hara et al. |
| 2009/0003125 A1 * | 1/2009 | Kusaka et al. .......... 366/160.1 |
| 2009/0038299 A1 * | 2/2009 | Gierszewski et al. ...... 60/301 |
| 2009/0107114 A1 * | 4/2009 | Ammineni et al. ........ 60/277 |
| 2010/0064664 A1 * | 3/2010 | Fokkelman .............. 60/276 |
| 2010/0179769 A1 * | 7/2010 | Zrilli .................... 702/24 |
| 2011/0000187 A1 * | 1/2011 | Elsasser et al. .......... 60/273 |
| 2011/0082622 A1 * | 4/2011 | Wehmeier et al. ........ 701/34 |
| 2012/0010786 A1 * | 1/2012 | Stickel et al. ............ 701/50 |
| 2012/0036838 A1 * | 2/2012 | Furuya .................. 60/285 |
| 2013/0028792 A1 | 1/2013 | Yano et al. |

FOREIGN PATENT DOCUMENTS

| | | |
|---|---|---|
| CN | 201903477 U | 7/2011 |
| CN | 102735803 A | 10/2012 |
| EP | 0409013 A3 | 10/1991 |
| JP | 63-191943 | 8/1988 |
| JP | 2001-013048 | 1/2001 |
| JP | 2003-028765 | 1/2003 |
| JP | 2003-149099 A | 5/2003 |
| JP | 2005-061913 | 3/2005 |
| JP | 2006-214949 | 8/2006 |
| JP | 2010-276473 | 12/2010 |
| JP | 2010-281668 | 12/2010 |
| JP | 2013-104670 | 5/2013 |
| WO | 2011125258 A1 | 10/2011 |

* cited by examiner

EXHAUST GAS ANALYSIS SYSTEM AND PROGRAM FOR THIS SYSTEM

CROSS-REFERENCE TO RELATED APPLICATION

This application claims priority to Japanese Patent Application No. 2011-246280 filed Nov. 10, 2011, the disclosure of which is incorporated in its entirety by reference herein.

FIELD

This invention relates to an exhaust gas analysis system that conducts an analysis of components contained in an exhaust gas discharged from, for example, an engine and a program for the exhaust gas analysis system used for this system.

BACKGROUND

As this kind of the exhaust gas analysis system there is an exhaust gas analysis system that measures carbon monoxide (CO), total hydrocarbons (THC), nitrogen oxide (NOx), and carbon dioxide (CO2) contained in an exhaust gas emitted from, for example, an engine of an automobile.

Concretely, the above-mentioned exhaust gas analysis system has an exhaust gas flow line where the exhaust gas of the engine flows, and a measurement device that is arranged in the exhaust gas flow line and that measures various components contained in the exhaust gas flowing in the exhaust gas flow line.

Conventionally as shown in the patent document 1, in order to remove the pollutant in the exhaust gas flow line in the upstream side of the measurement device, a purge is conducted by supplying a large amount of a clean purge gas in a pressurized state to the exhaust gas flow line in the upstream side of the measurement device so as to remove a residual material (pollutant component) that attaches to or resides in each part of the exhaust gas flow line after measuring the exhaust gas for the above-mentioned exhaust gas analysis system.

However, there is a problem that there is a user who forgets to conduct the purge after measuring the exhaust gas. In addition, there is a problem that there is a user who does not conduct the purge because the user considers there is no problem even though the purge is not conducted every time the exhaust gas measurement is completed if an error of the exhaust gas measurement is negligibly small. As mentioned, if the exhaust gas measurement is conducted without conducting the purge after completion of the exhaust gas measurement, a measurement error generates because the pollutant component that attaches to or resides in the exhaust gas flow line at a time of a previous exhaust gas measurement is measured in the following exhaust gas measurement. In addition, it is difficult to objectively judge whether the measurement error is negligibly small or not so that it is not possible to judge whether the measured concentration of the pollutant component is due to increase of the concentration of the pollutant component contained in the exhaust gas or the measured concentration of the pollutant component is due to the pollutant component that attaches to or resides in the line.

As mentioned, it is a situation that whether the purge is necessary to be conducted or not is judged objectively by a user and that the purge is conducted every time the exhaust gas measurement is completed is considered to be the most reliable method to reduce the measurement error. In other words, the user selects arbitrarily whether the purge is conducted every time the exhaust gas measurement is completed or not by comparing a merit that the measurement error is reduced due to conducting the purge with a demerit that a number of operation increases due to conducting the purge.

SUMMARY

A main object of this invention is to urge a user to conduct a purge in an exhaust gas flow line by not only informing the user of the timing that the purge is necessary from the exhaust gas analysis system but also making it easy for the user to recognize the information. More specifically, the exhaust gas analysis system in accordance with this invention comprises an exhaust gas flow line where an exhaust gas flows, a measurement device that is arranged in the exhaust gas flow line and that includes a pollutant component meter to measure a pollutant component to be a cause of pollutant of the exhaust gas flow line, and a display control device that compares a measurement signal value obtained by the pollutant component meter or its arithmetic value with a predetermined pollutant tolerance and that displays a warning window on a display in case that the measurement signal value or the arithmetic value exceeds the pollutant component tolerance.

In accordance with this arrangement, since warning is issued in case that the measurement signal value obtained by the pollutant component meter or its arithmetic value exceeds the predetermined pollutant tolerance, it is possible to inform the user of the timing that the purge is necessary. In addition, at this time, since the warning window is displayed on the display, the user can visually recognize the timing that the purge is necessary. As a result of this, in accordance with this invention, it is possible to urge the user to conduct the purge at an appropriate timing. In case that the display displays the measurement result of the measurement device, since the user watches the display without fail, the warning window is watched by the user as well as the measurement result. This arrangement contributes to further enhancement of the effect of this invention.

Total hydrocarbons (THC) as being an absorbent component are conceived as a main cause of the measurement error of the exhaust gas measurement by being absorbed to and residing in the exhaust gas flow line. Then it is preferable that the pollutant component meter is a THC meter that measures a concentration of THC in the exhaust gas flowing in the exhaust gas flow line.

A pollutant degree of the exhaust gas flow line to be purged varies depending on an object or a usage of the exhaust gas measurement. Then in order to make it possible to arbitrarily set a standard of the warning to urge the purge by a user, it is preferable that the display control device displays a warning set window to set the pollutant tolerance and sets a numerical value input on the warning set window as the pollutant tolerance.

The pollutant component as being the cause of the pollutant in the exhaust gas flow line varies depending to a kind of the exhaust gas to be measured. Then, it is preferable that the warning set window is to set not only the pollutant tolerance but also the kind of the pollutant component, and the display control device sets the component input on the warning set window as the pollutant component. Namely, it is possible for the user to arbitrarily set the kind of the pollutant component and the component tolerance of the pollutant component through the warning set window.

As an exhaust gas analysis system there is an exhaust gas analysis system having a plurality of exhaust gas flow lines, and the measurement device is arranged on each of the exhaust gas flow lines respectively. For the exhaust gas analysis system having this arrangement, it is preferable that the warning set window is so configured to be able to set the pollutant tolerance for each of the exhaust gas flow lines respectively. With this arrangement, it is possible to set the pollutant tolerance for each of the multiple exhaust gas flow lines respectively on a single window.

A pollutant component accumulates little by little in the exhaust gas flow line by flowing the exhaust gas containing the pollutant component in the exhaust gas flow line. Then it is possible to estimate a pollutant degree of the exhaust gas flow line based on how much the exhaust gas containing the pollutant component flows in the exhaust gas flow line. As a result of this, it is conceivable that the arithmetic value is set as an accumulated value obtained by accumulating the measurement signal values obtained by the pollutant component meter. Under this condition, if the measurement signal value obtained by the pollutant component meter is continuously accumulated, the accumulated value becomes too big. Then since it becomes difficult to set the pollutant tolerance, it is preferable that the arithmetic value is an integrated value obtained by accumulating the measurement signal values obtained at predetermined sampling intervals.

Like cases of examining a high performance sports car or conducting an examination in a high-revolution and high-load condition, there is a case that the concentration of the discharged pollutant component (for example, concentration of THC) is extremely high.

In case of comparing the exhaust gas whose pollutant component concentration is high with the exhaust gas whose pollutant component concentration is low, even though the accumulated value of the pollutant component is the same, it is considered that much more pollutant substances attach to the exhaust gas flow line for the exhaust gas having the high pollutant component concentration. In this case, it is preferable both to conduct the purge as soon as possible and to intensely clean inside of the exhaust gas flow line.

In order to make it possible for a user to grasp the situation without fail and to prevent degradation of the measurement accuracy or failure of the measurement device as much as possible due to contamination of the pollutant substance, it is preferable that a warning content displayed on the warning window varies according to an arrival time to the tolerance as being a time from the integrated value is zero to the integrated value exceeds the pollutant tolerance.

Concretely, it is preferable to set that the shorter the arrival time to the tolerance is, the higher the level of importance of the warning content is.

It is preferable to change not only the warning content but also the following cleaning operation according to a difference of the arrival time to the tolerance. In order to make it possible for a user to select the appropriate operation among various cleaning operations and to conduct the appropriate cleaning operation easily, a cleaning operation guide window to remove the pollutant is displayed after the warning window is displayed and the cleaning operation indicated by the cleaning operation guide window is so arranged to vary according to the arrival time to the tolerance.

It is preferable that the display control device displays a log display window showing display log information of the warning window. The display log information of the warning window is a time and a date when the warning window is displayed. With this arrangement, since not only the time and the date when the warning window is displayed but also the frequency of displaying the warning window can be made clear, it is possible to verify that the purge has been appropriately conducted back to the past.

In addition, a program for an exhaust gas analysis system in accordance with this invention is a program for an exhaust gas analysis system used for an exhaust gas analysis system having an exhaust gas flow line where an exhaust gas flows and a measurement device that is arranged in the exhaust gas flow line and that contains a pollutant component meter to measure a pollutant component as being a cause of the pollutant in the exhaust gas flow line, and is characterized by producing a warning display function that compares a measurement signal value obtained by the pollutant component meter or its arithmetic value with a predetermined pollutant tolerance and that displays a warning window on a display in case that the measurement signal value or the arithmetic value exceeds the predetermined pollutant component tolerance.

In accordance with this invention having the above arrangement, it is possible to urge a user to conduct a purge in an exhaust gas flow line by not only informing the user of the timing that the purge is necessary from the exhaust gas analysis system but also making it easy for the user to recognize the information.

DETAILED DESCRIPTION

An exhaust gas analysis system 100 in accordance with this invention will be explained with reference to drawings.

Figure 1:
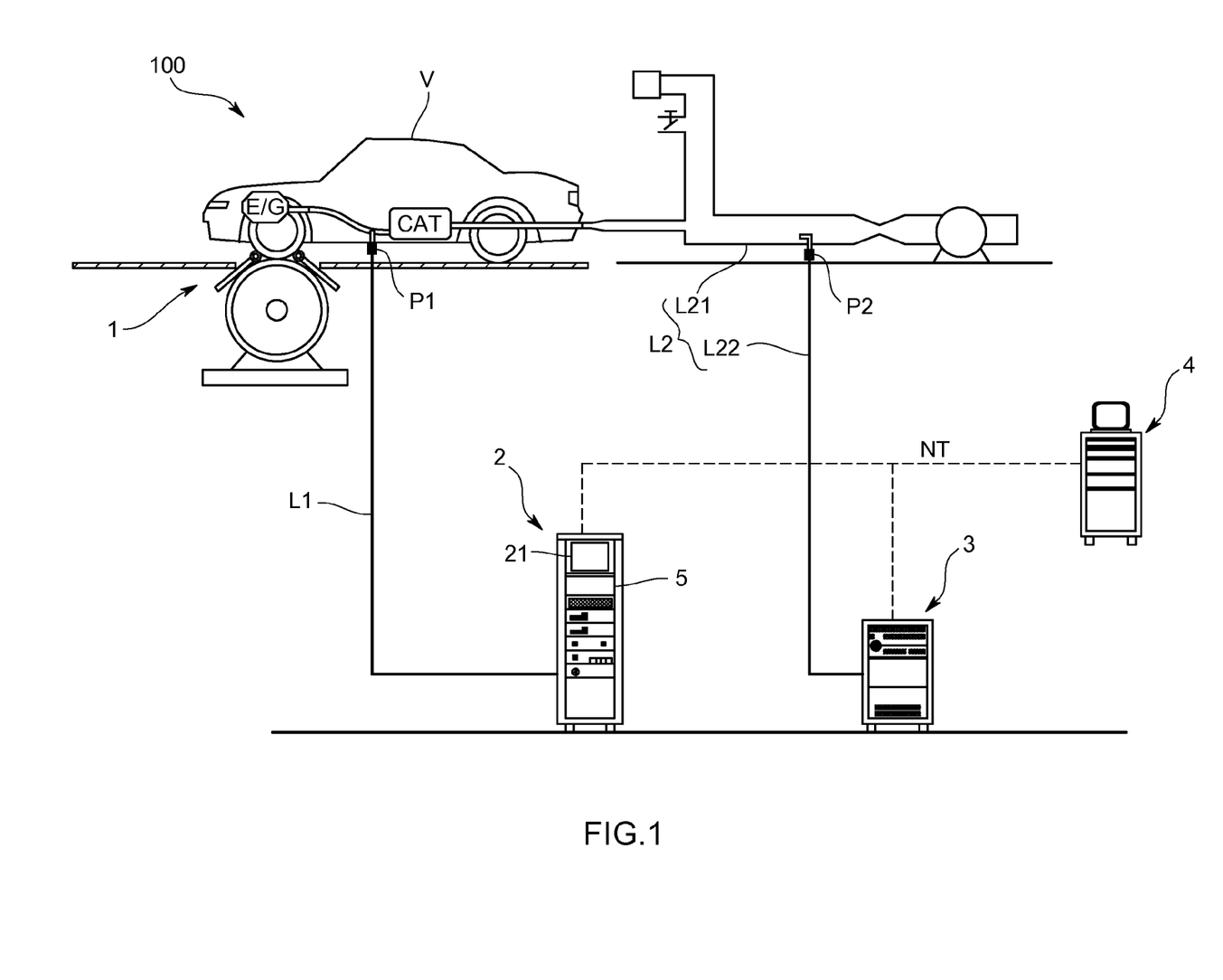
FIG. 1 is a pattern diagram showing a configuration of an exhaust gas analysis system in accordance with one embodiment of this invention.

The exhaust gas analysis system 100 of this embodiment is to measure an exhaust gas of an automobile (V) in a mom so-called test cell and, as its overall configuration is shown in FIG. 1, has a chassis dynamo device 1 on which the automobile (V) as being a test specimen is loaded, a first exhaust gas measurement device 2 and a second exhaust gas measurement device 3 that analyze various components contained in the exhaust gas emitted from an engine of the automobile (V), an exhaust gas flow line (L) that introduces the exhaust gas emitted from the engine into the first exhaust gas measurement device 2 and the second exhaust gas measurement device 3, and a center information processing unit 4 that gives and receives data between a dynamo control device (not shown in drawings) that controls the chassis dynamo device 1 and the first exhaust gas measurement devices 2, and the second exhaust gas measurement device 3. In addition, the exhaust gas analysis system 100 is installed on a drivers seat of the automobile (V), and has an automatic driving mechanism (not shown in drawings) comprising a driving arm that mechanically drives an accelerator, a brake, a shift lever, and a handle and an automatic driving mechanism control device (not shown in drawings) that drives the automatic driving mechanism. The exhaust gas analysis system 100 drives the driving arm based on a control signal from the outside so as to automatically run the automobile (V) on the chassis dynamo device 1.

The exhaust gas flow line (L) comprises a first exhaust gas flow line L1 to introduce the exhaust gas emitted from the engine into the first exhaust gas measurement device 2 without diluting the exhaust gas and a second exhaust gas flow line L2 to introduce the exhaust gas, as being the exhaust gas from the engine, emitted from an exhaust duct (a tail pipe) after passing a catalyst (CAT) with diluting the exhaust gas by means of a dilution tunnel L21.

The first exhaust gas flow line L1 is a direct sampling line that directly sample the engine exhaust gas with one end having an introducing port P1 that is arranged on the exhaust duct and that introduces the engine exhaust gas emitted from the engine and the other end connected to a connecting port (not shown in drawings) of the first exhaust gas measurement device 2.

In addition, the second exhaust gas flow line L2 comprises a dilution tunnel L21 that is connected with the exhaust duct of the automobile (V) and that dilutes the engine exhaust gas with air, and a dilution sampling line L22 with one end having an introducing port P2 to introduce the diluted exhaust gas and the other end connected to a connection port (not shown in drawings) of the second exhaust gas measurement device 3.

The first exhaust gas measurement device 2 is loaded with a plurality of gas analyzers whose measurement principle differs each other so that it is possible to continuously and respectively measure each component such as CO, CO2, O2, HC, THC, CH4, NO, NOx contained in the engine exhaust gas. For example, the first exhaust gas measurement device 2 has an infrared gas analyzer using a non-dispersive infrared absorption method (NDIR) to measure concentrations of CO, CO2, HC, and NO, a NOx meter using a chemiluminescent method (CLD) to measure a concentration of NOx, an O2 meter using a magnetic pressure method (PMD) to measure a concentration of O2, a THC meter using a heater-type hydrogen flame ionization detecting method (HFID) to measure a concentration of THC, and a CH4 meter using a gas chromatograph/hydrogen flame ionization detector (GC-FID) to measure a concentration of CH4. In this embodiment, THC is the pollutant component that is absorbed into the exhaust gas flow line (L).

The first exhaust gas measurement device 2 comprises a computer system that makes use of a CPU, a memory or the like, and has a function of being able to interactively communicate a control signal or data from outside.

The second exhaust gas measurement device 3 is loaded with a plurality of gas analyzers whose measurement principle differs each other so that it is possible to continuously and respectively measure each component such as THC, CH4, and NO contained in the diluted exhaust gas. For example, the second exhaust gas measurement device 3 has an infrared gas analyzer using a non-dispersive infrared absorption method (NDIR) to measure a concentration of NO, and a THC meter using a heater-type hydrogen flame ionization detecting method (HFID) to measure a concentration of THC, and a CH4 meter using a gas chromatograph/hydrogen flame ionization detector (GC-FID) to measure a concentration of CH4. In this embodiment, THC is the pollutant component that is absorbed into the exhaust gas flow line (L).

The second exhaust gas measurement device 3 comprises a computer system that makes use of a CPU, a memory or the like, and has a function of being able to interactively communicate a control signal or data from outside.

The center information processing unit 4 is a computer system comprising, for example, a CPU, a memory, a communication interface, a display and an input device, and has a function of a server. The center information processing unit 4 makes it possible to control each control device, and the first and the second exhaust gas measurement devices 2, 3 or to administrate data by giving and receiving the data between each control device and the first and second exhaust gas measurement devices 2, 3 through a network (NT) such as LAN.

When necessary parameters such as vehicle information and a driving mode is given to the center information processing unit 4, the chassis dynamo device 1 and the automatic driving mechanism are controlled by its control device respectively, the automobile (V) (vehicle) runs in a desired mode, the exhaust gas data is automatically measured by activating the first and the second exhaust gas measurement devices 2, 3, and the exhaust gas data and the running data are administrated in an integrated manner by the center information processing unit 4.

The center information processing unit 4, each control device and the first and the second exhaust gas measurement devices 2, 3 are not necessarily arranged in an physically independently dispersed manner as shown in FIG. 1, and it is a matter of course that a part or all of them may be integrally arranged.

With this arrangement, for the exhaust gas analysis system 100 of this embodiment, the first exhaust gas measurement device 2 has the display control device 5 that controls a window display of a display 21 of the first exhaust gas measurement device 2.

Figure 2:
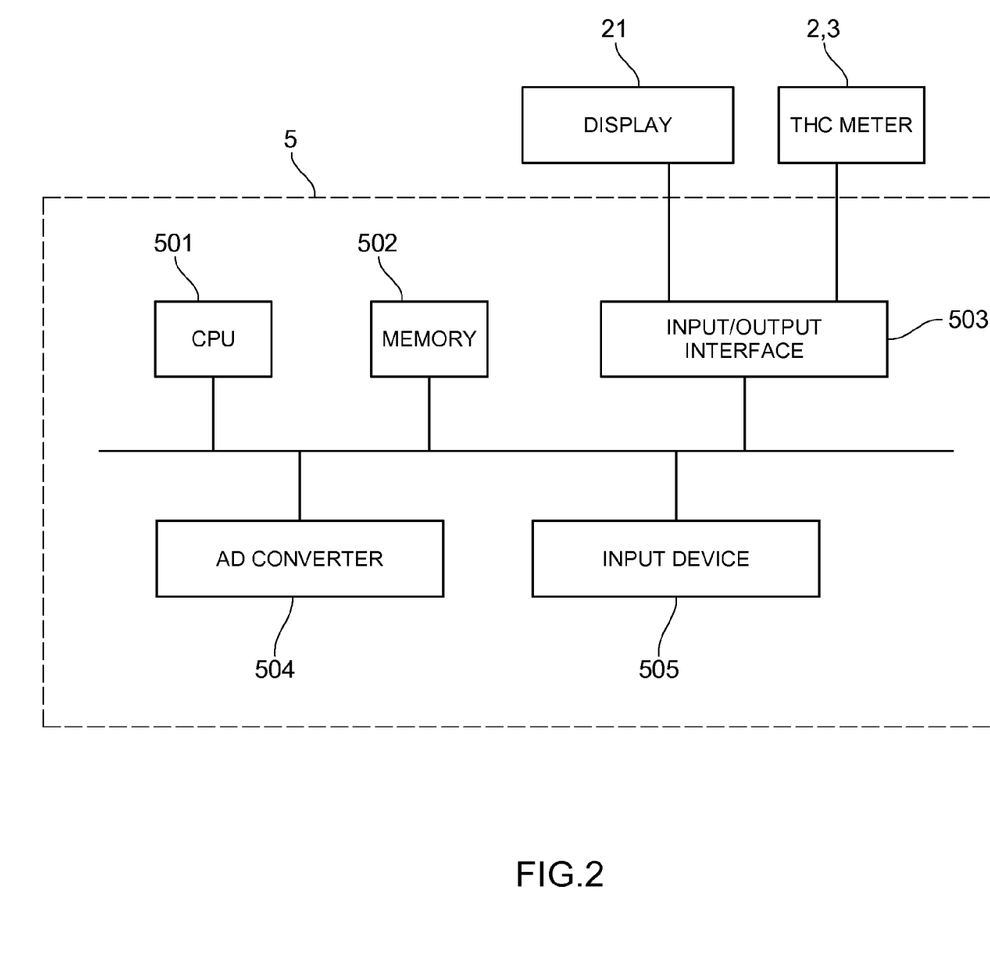
FIG. 2 is a device configuration diagram of a display control device of this embodiment.
Figure 3:
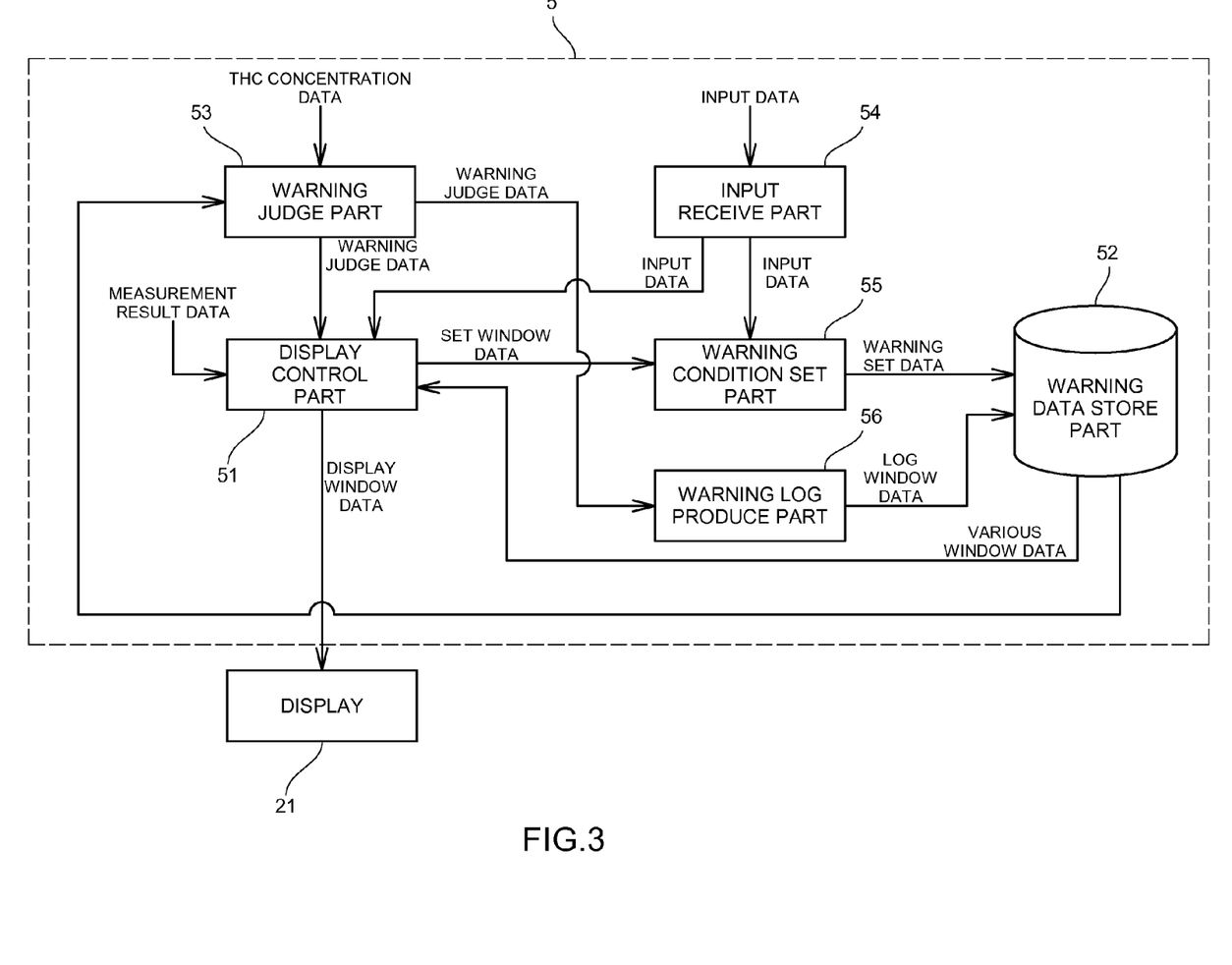
FIG. 3 is a function configuration diagram of the display control device of this embodiment.

The display control device 5 is, as shown in FIG. 2, a general-purpose or dedicated computer comprising a CPU 501, a memory 502, an input/output interface 503, an AD converter 504 and an input device 505. The display control device 5 functions, as shown in FIG. 3, as a display control part 51, a warning data store part 52, a warning judge part 53, an input receive part 54, a warning condition set part 55 and a warning log produce part 56 by cooperating the CPU 501 and its peripheral devices based on predetermine programs stored in a predetermined area of the memory 502.

The display control part 51 has a measurement result display mode to display a measurement result display window showing a measurement result obtained by each gas analyzer of the first exhaust gas measurement device 2 and a purge relating mode to display a window relating to the purge of the exhaust gas flow line (concretely, the direct sampling line L1 and the dilution sampling line L22).

The measurement result display mode is a mode to display a measurement result obtained by each gas analyzer of the first exhaust gas measurement device 2 and is a display function of the ordinary first exhaust gas measurement device 2.

Meanwhile, the purge related mode is a mode to display a window relating to the purge of the direct sampling line L1 connected to the first exhaust gas measurement device 2 and the dilution sampling line L22 connected to the second exhaust gas measurement device 3. Not only the purge related mode can be initiated in a state that the measurement result display mode is not initiated but also the purge related mode can be initiated together with the measurement result display mode while the measurement result display mode is initiated. As mentioned above, the first exhaust gas measurement device 2 not only displays the result from the first exhaust gas measurement device 2 but also displays the window relating to the purge of the second exhaust gas measurement device 3.

Hereinafter, the purge related mode will be explained together with the function of each part of the display control device 5 with reference to FIG. 3~FIG. 8.

Figure 4:
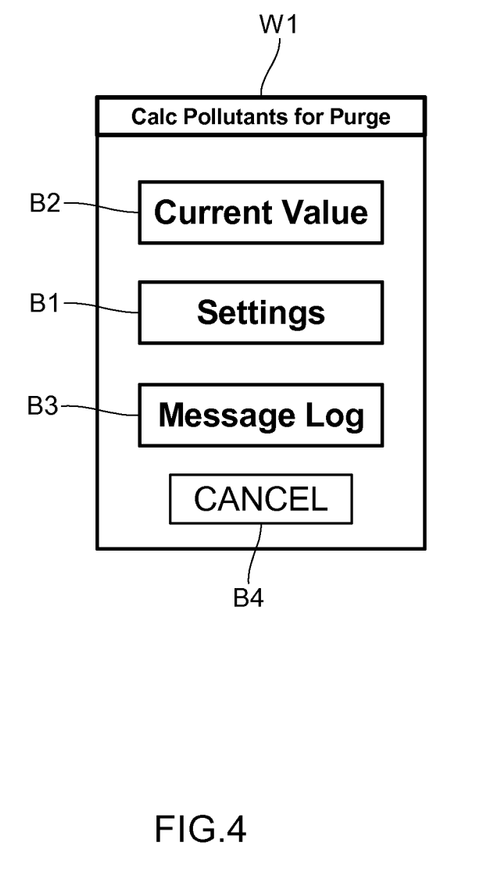
FIG. 4 is a view showing a purge selection window of this embodiment.

First, the display control part 51 displays a purge selection window W1 shown in FIG. 4 on the display 21 in the purge related mode. The window data showing the purge selection window W1 is stored in the warning data store part 52.

Figure 7:
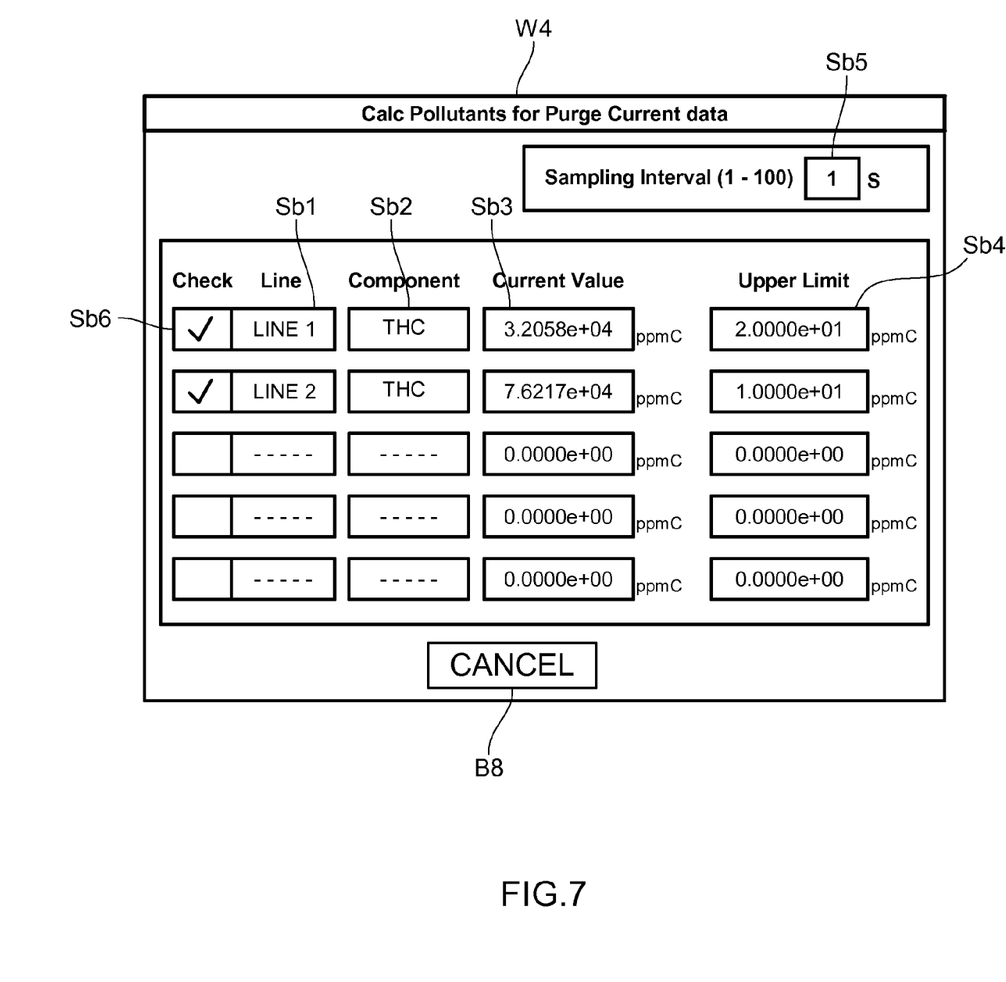
FIG. 7 is a view showing a current value display window of this embodiment.
Figure 8:
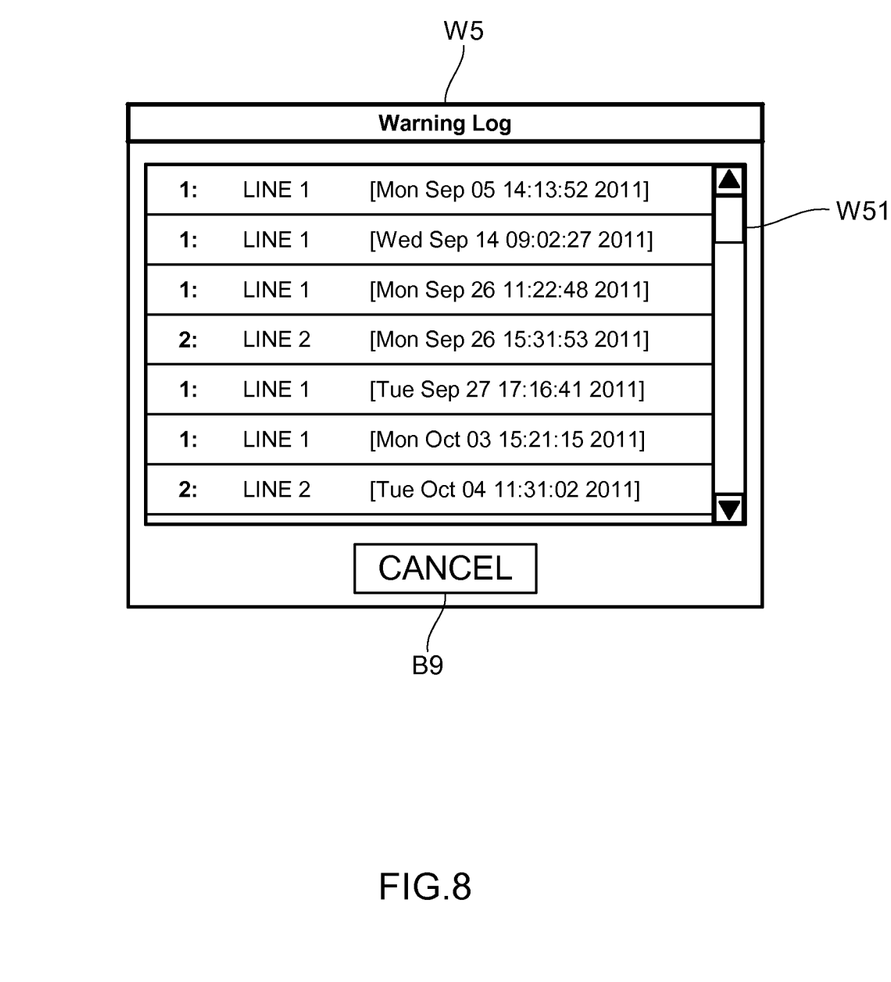
FIG. 8 is a view showing a log display window of this embodiment.

The purge selection window W1 is a window to selectively display various display windows relating to the purge, and contains (1) a warning set window button ("Settings") B1 to display the warning set window W2 (refer to FIG. 5) to set the pollutant tolerance or the like, a current value display window button ("Current Value") B2 to display a current value display window W4 (refer to FIG. 7) displaying an accumulated value of the measurement signal values obtained by the pollutant component meter (the THC meter in this embodiment), and a warning log window button ("Message Log") B3 to display the warning log window W5 (refer to FIG. 8). A cancel button ("CANCEL") B4 to close the purge selection window W1 is also displayed.

In a state that the purge selection window W1 is displayed, when a user clicks either one of the buttons B1~B4 by means of the input device 50 such as a mouse, a button selection data as being the input data is received by the input receive part 54. Then the button selection data is sent to the display control part 51.

The display control part 51 that obtains the button selection data obtains a window data showing a window selected by the button selection data from the warning data store part 52, and then displays the obtained window data on the display 21. Hereinafter, cases wherein each window is selected will be explained.

Figure 5:
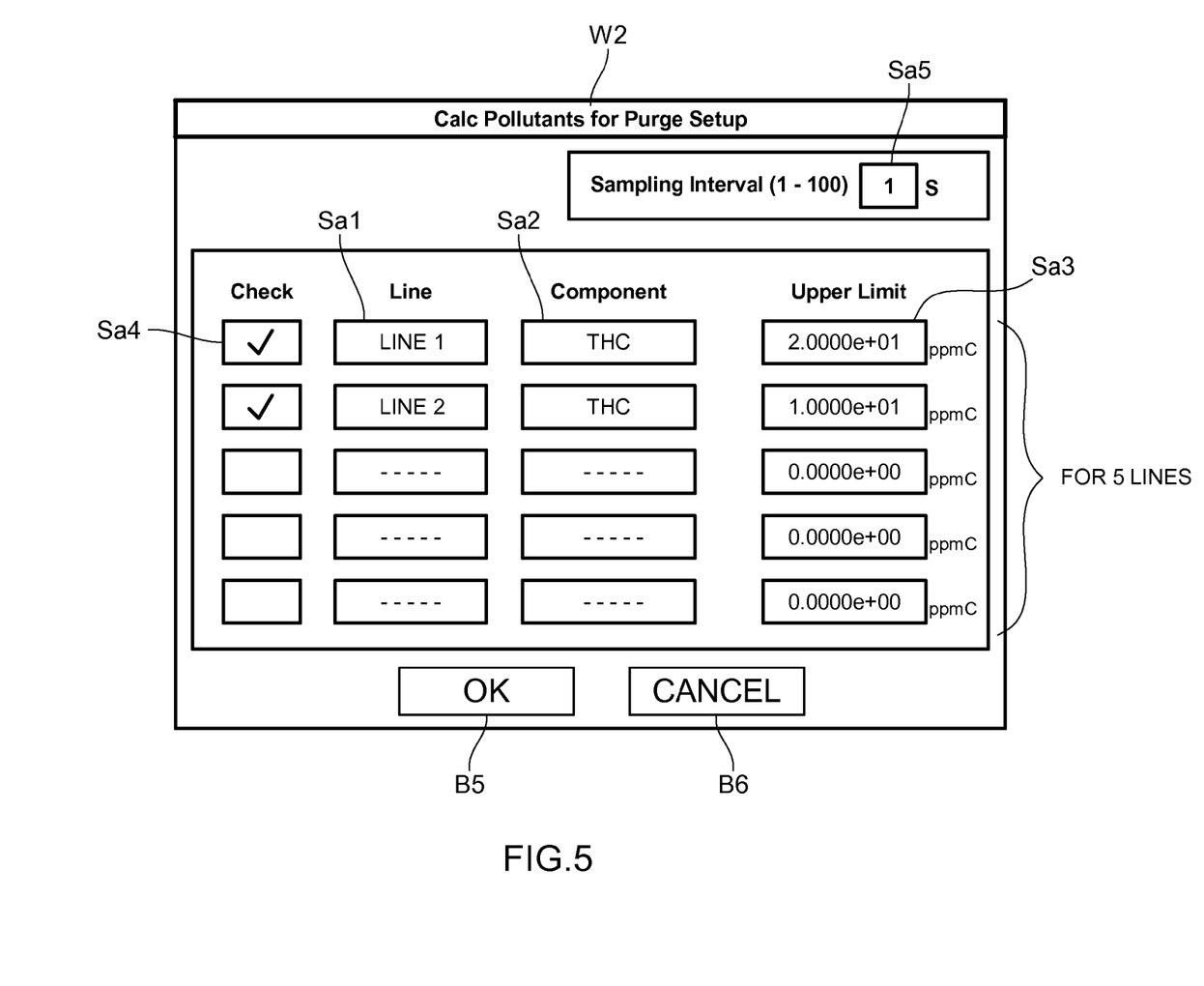
FIG. 5 is a view showing a warning set window of this embodiment.

In case that the warning set window button B1 is selected by the user, the display control part 51 obtains the warning set window data showing the warning set window W2 from the warning data store part 52, and displays the warning set window W2 shown in FIG. 5 on the display 21.

The warning set window W2 is a window to set each pollutant tolerance and a kind of the pollutant component for the multiple exhaust gas flow lines (concretely, the direct sampling line L1 and the dilution sampling line L22) and has a line selection item input field ("Line") Sa1 to select the exhaust gas flow line L1, L22, a pollutant component item input field ("Component") Sa2 to set the pollutant component, and a pollutant tolerance item input field ("Upper Limit") Sa3 to set the pollutant tolerance of the pollutant component. The pollutant tolerance in this embodiment is an upper limit of the accumulated value of the pollutant component concentration. These input fields Sa1~Sa3 are provided for each of the multiple lines in order to enable each setting for each of the multiple exhaust gas flow lines L1, L22 respectively. In this embodiment, as shown in FIG. 5, the warning set is enabled for a maximum of five lines, and shown is a case that the pollutant component and the pollutant tolerance are set for the line 1 and the line 2. The line 1 is the direct sampling line L1 and the line 2 is the dilution sampling line L22. The pollutant component is the THC in either case. As mentioned, in this embodiment, it is possible for a single warning set window W2 to set the pollutant component and its pollutant tolerance for each of the multiple exhaust gas flow lines individually.

In addition, a selection field ("CHECK") Sa4 to select whether the warning is conducted for the line input by the user or not is also displayed on the warning set window W2. In case that the selection field Sa4 is not provided, when a numerical value or a component is input to each field Sa1~Sa3, the warning may be conducted for the line to which input is conducted.

A line name that can be input to the line selection item input field Sa1 is previously related to the exhaust gas flow line (concretely, the direct sampling line L1 and the dilution sampling line L22) constituting the exhaust gas analysis system 100. A pollutant component name that can be input to the pollutant component item input field Sa2 is previously related to the gas analyzer included in the measurement device (concretely, the first exhaust gas measurement device 2 and the second exhaust gas measurement device 3) of the exhaust gas analysis system 100.

In addition, the warning set window W2 has a sampling interval item input field Sa5 to set a sampling interval when the measurement signal is obtained from the pollutant component meter (the THC meter) in order to calculate the accumulated value of the pollutant component concentration. The sampling interval item input field Sa5 is configured to set the sampling interval within a range between 1 second and 100 seconds, however, it is not limited to this.

The warning set window W2 contains a determination button ("OK") B5 to determine the warning setting and a cancel button ("CANCEL") B6 to cancel the warning seeing and to close the warning set window W2.

In a state that the warning set window W2 is displayed, when the user inputs a specific line name (for example, the line 1) into the line selection item input field Sa1, a specific component name (for example, the THC) into the pollutant component item input field Sa2, a specific numerical value (for example, 2.0000e+01) into the pollutant tolerance item input field Sa3, and a specific numerical value (for example, 1) into the sampling interval item input field Sa5 and clicks the determination button B5 of the warning set window W2, the condition input into these input fields Sa1~Sa5 is determined and these input data is received by the input receive part 54. Then the input receive part 54 sends these input data to the warning condition set part 55. Later, the warning condition set part 55 stores the numerical value and the component input into each input field Sa1~Sa5 as the warning condition data in the warning data store part 52. The warning condition data stored in the warning data store part 52 is obtained by the warning judge part 53.

When the warning judge part 53 obtains the warning condition data, the warning judge part 53 obtains the THC concentration data from the THC meter arranged on the exhaust gas flow line (L1 and L22) that is selected at a time of measuring the exhaust gas, and then compares the arithmetic value of the THC concentration data with the pollutant tolerance shown by the warning condition data. The warning judge part 53 obtains the THC concentration data at the timing interval (Sampling Interval) shown by the warning condition data from the THC meter, and the obtained THC concentration is accumulated and the accumulated THC concentration is set as the arithmetic value. The warning judge part 53 outputs the accumulated value data to the display control part 51.

In addition, the warning judge part 53 compares the accumulated value of the THC concentration with the predetermined pollutant tolerance. In case that the accumulated value exceeds the pollutant tolerance, the warning judge part 53 outputs the warning judge data to the display control part 51. Then when the display control part 51 obtains the warning judge data, the display control part 51 obtains the warning window data from the warning data store part 52 and displays the warning window W3 shown in FIG. 6 on the display 21.

Figure 6:
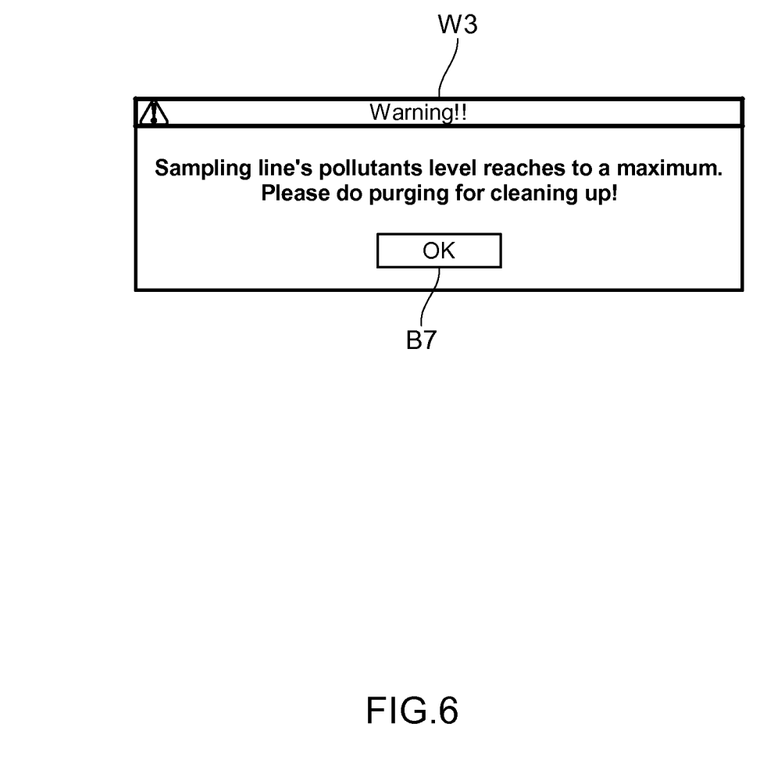
FIG. 6 is a view showing a warning window of this embodiment.

The warning window W3 is displayed in a case that the accumulated value exceeds the upper limit value (the pollutant tolerance). The warning window W3 is a window of a content that recommends the purge be conducted so as to purge the exhaust gas flow line (the sampling line L1 or L22) because the pollutant component of the exhaust gas flow line (the sampling line L1 or L22) reaches the upper limit value. The OK button B7 is provided for the warning window W3. The warning window W3 disappears when the user clicks this OK button B7. Even though the exhaust gas analysis system 100 is in operation of measurement, the warning window W3 is displayed together on the measurement result display window without ceasing the measurement operation. When the OK button B7 is clicked, the warning window W3 is closed on the display 21 and also subsequently the usual exhaust gas measurement can be continued.

In the above arrangement, in case that the accumulated value of the THC concentration exceeds the upper limit value (the pollutant tolerance) while measuring the exhaust gas, the warning window W3 is displayed. However, in case that the accumulated value of the THC concentration in the last measurement of the exhaust gas (in case that the accumulated value exceeds the upper limit prior to initiation of the exhaust gas measurement at this time), the warning window W3 is displayed at a time of initiating the exhaust gas measurement.

In case that the purge is conducted, the warning judge part 53 obtains an input signal (for example, a signal input by the user or a signal received from a device acting for purge in case of conducting the purge) showing that the purge is conducted and resets the accumulated value of the THC concentration to zero.

Furthermore, the warning judge part 53 outputs the warning judge data to the warning log produce part 56. The warning log produce part 56 that has obtained the warning judge data produces a log window data showing the line on which the warning window is displayed and a time and a date when the warning window is displayed and stores the log window data in the warning data store part 52.

Next, in case that the current value display window button B2 is selected by the user, the display control part 51 obtains the current value display window data showing the current value display window W4 from the warning data store part 52 and displays the warning set window W2 shown in FIG. 7 on the display 21.

The current value display window W4 is a window that displays the accumulated value of the measurement signal value obtained by the THC meter, and has a line display field ("Line") Sb1 showing a line to which the warning set is conducted, a pollutant component display field ("Component") Sb2 showing a pollutant component set in the line, an accumulated value display field ("Current Value") Sb3 displaying the accumulated value of the measurement signal value obtained by the THC meter, a pollutant tolerance display field ("Upper Limit") Sb4 showing the pollutant tolerance set for the line, a sampling interval display field ("Sampling Interval") Sb5 showing the sampling interval set for calculating the accumulated value, and a selection line display field ("CHECK") Sb6 displaying the line to which the warning is issued. The current value display window W4 has a button ("CANCEL") B8 to close the current value display window W4.

The display control part 51 displays the line, the component and the numerical value set by the warning set window W2 in the line display field Sb1, the pollutant component display field Sb2, the pollutant tolerance display field Sb4 and the sampling interval display field Sb5, and displays, for example, the accumulated value output by the warning judge part 53 in the accumulated value display field Sb3. Since the display control part 51 also obtains the THC concentration data from the THC meter, the accumulated value calculated by the display control part 51 may be displayed. As mentioned, since the current value display window W4 is displayed, it is possible for the user to watch the accumulated value at a time when the current value display window W4 is displayed so that the user can anticipate a period of time until the warning will be displayed.

Next, in case that the warning log window button B3 is selected by the user, the display control part 51 obtains the warning log window data showing the warning log window W5 from the warning data store part 52 and displays the warning log window W5 shown in FIG. 8 on the display 21.

The warning log window W5 displays the log of the warnings that have been issued in the past by a list, and displays the chronological log information that shows each warning window W3 in a state that the latest log information is displayed in the most downside of the display 21 sequentially. The line to which the warning is issued, the day of the weak, the month, the date, and the time when the warning is issued are displayed in a single line from the left to the right as the log information of the warning window W3. With this arrangement, since not only the time and the date when the warning window W3 is displayed but also the frequency of displaying the warning window W3 can be made clear, it is possible to verify that the purge has been appropriately conducted back to the past. In case that the warning logs are too many to be displayed in the warning log window W5, a scroll bar W51 is displayed in a side corner of the warning log window W5 and the warning log displayed on the warning log window W5 can be moved by operating a knob of a scroll bar W51. With this operation, it is possible to verify the warning log that has not been displayed on the warning log window W5 back to the past. The warning log window W5 has a button ("CANCEL") to close the warning log window W5.

In accordance with the exhaust gas analysis system 100 in accordance with this embodiment having the above-mentioned arrangement, since the warning is issued in case that the accumulated value of the measurement signal value obtained by the pollutant component meter exceeds the predetermined pollutant tolerance, it is possible to inform the user of the timing that the purge is necessary. In addition, at this time when the accumulated value exceeds the predetermined pollutant tolerance, since the warning is displayed on the display 21, the user can visually recognize the timing that the purge is necessary. As a result of this, in accordance with this embodiment, it is possible to urge the user to conduct the purge at an appropriate timing. In addition, in accordance with this embodiment, since the warning window is displayed on the display 21 that displays the measurement result of the exhaust gas, it is possible for the user to visually recognize the warning window without fail. Then the purge is furthermore promoted.

The present claimed invention is not limited to the above-mentioned embodiment.

For example, the warning content displayed on the warning window may vary in proportion to a length of the arrival time to the tolerance as being a period from a time when the accumulated value is 0 to a time when the accumulate value exceeds the pollutant tolerance.

More specifically, that the arrival time to the tolerance is short indicates that the pollutant component concentration of the flowing exhaust gas is high. In case of comparing the exhaust gas having the high pollutant component concentration with the exhaust gas having the low pollutant component concentration, even though the accumulated value of the pollutant component is the same, it is considered that much more pollutant substances attach to the exhaust gas flow line for the exhaust gas having the high pollutant component concentration. In this case, it is preferable both to conduct the purge as soon as possible and to intensely clean the inside of the exhaust gas flow line.

Figure 9:
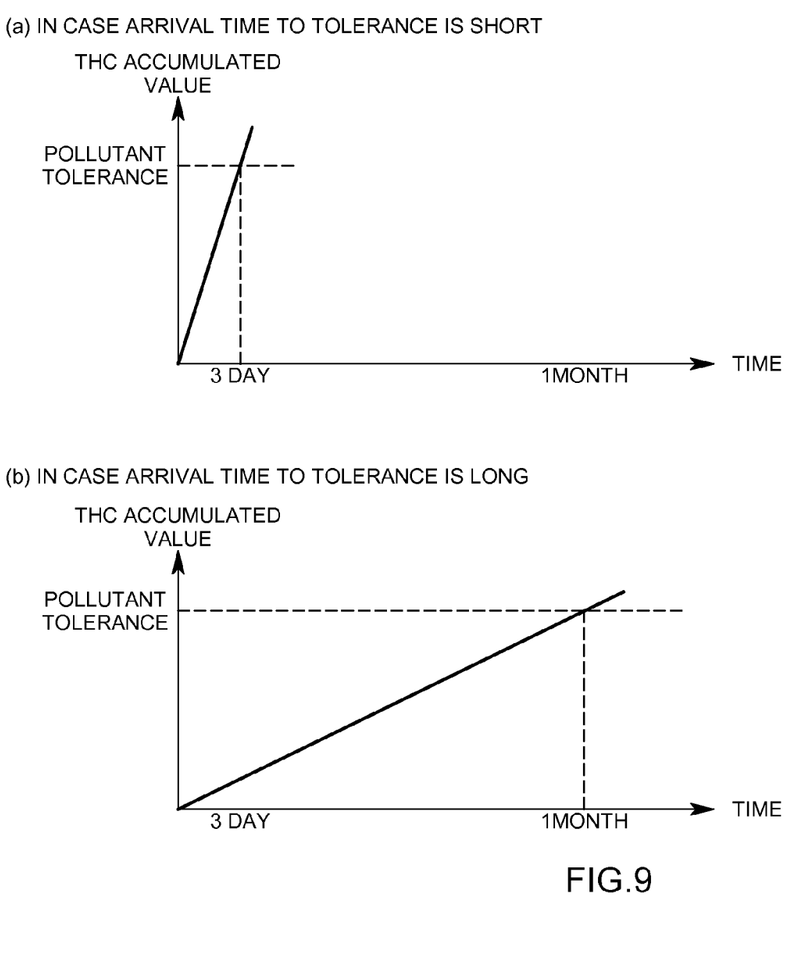
FIG. 9 is a graph showing an over time change of an accumulated concentration of THC in the other embodiment of this invention.

Then, the shorter the arrival time to the tolerance is, it is preferable to display a notice that, for example, a more immediate purge is required or a more intense purge (for example, a heat purge) is recommended as the warning content. With this arrangement, it is possible for the user to grasp the situation without fail and to prevent degradation of the measurement accuracy or failure of the measurement device due to contamination as much as possible. At this time, it is more preferable that an over time change graph of the pollutant substance accumulated value (for example, the accumulated value of the THC) as shown in FIG. 9 is displayed on the warning window.

In addition, after displaying the warning window, a cleaning operation guide window (not shown in drawings) to instruct an operation of removing the pollutant may be displayed. Concretely, a guide button may be arranged on the warning window and the user can click the guide button so that the cleaning operation guide window is displayed.

Furthermore, if it is so set that the shorter the arrival time to the tolerance, the more intense the contents of the cleaning operation to be instructed is displayed in the cleaning operation guide window, it is possible to urge the user to conduct the pollutant removing operation without fail. For example, it can be conceived that a default value of a kind of the purge is set as a more intense heating purge, a default value of a purge period is set to be longer than usual, or a process of the purge operation itself is changed.

Furthermore, a plurality of levels of the pollutant tolerance may be provided and a warning level of the warning window is changed depending on the pollutant tolerance level. The warning level includes, for example, a level (a notification level) indicating that the pollutant removal may be conducted as soon as possible although the performance of the measurement device is sufficiently produced, a level (a precaution level) indicating that the pollutant removal is immediately necessary, and a level (an alarm level) indicating an abnormal state or a forced termination of the operation.

In addition, the first exhaust gas measurement device has the display control device 5 having the purge relating mode in the above-mentioned embodiment, however, the second exhaust gas measurement device may have the display control device 5. Furthermore, the center information processing unit 4 may have the display control device 5 having the purge relating mode.

In addition, the present claimed invention is not limited to the above-mentioned embodiment and may be variously modified without departing from a spirit of the invention.

EXPLANATION OF CODES

100 . . . exhaust gas analysis system
L . . . exhaust gas flow line
L1 . . . first exhaust gas flow line (direct sampling line)
L2 . . . second exhaust gas flow line
L21 . . . dilution tunnel
L22 . . . dilution sampling line
2 . . . first exhaust gas measurement device (measurement device)
21 . . . display
3 . . . second exhaust gas measurement device (measurement device)

5 . . . display control device
W2 . . . warning set window
W3 . . . warning window
W4 . . . current value display window
W5 . . . warning log window

The invention claimed is:
1. An exhaust gas analysis system comprising:
an exhaust gas flow line where an exhaust gas flows;
a measurement device that is arranged in the exhaust gas flow line and that includes a pollutant component meter to measure a pollutant component to be a cause of pollutant of the exhaust gas flow line; and
a display control device that compares an accumulated value, that is obtained by accumulating measurement signal values from the pollutant component meter at predetermined sampling intervals and is only reset to zero when a purge is conducted, with a predetermined pollutant tolerance at a time of measuring the exhaust gas and that displays on a display a warning window that recommends a purge be conducted in response to the accumulated value exceeding the pollutant tolerance.

2. The exhaust gas analysis system described in claim 1, wherein
a warning content displayed on the warning window varies according to an arrival time to the tolerance as being a time from the accumulated value is zero to the accumulated value exceeds the pollutant tolerance.

3. The exhaust gas analysis system described in claim 2, wherein
the shorter the arrival time to the tolerance is, the higher the level of importance of the warning content is.

4. The exhaust gas analysis system described in claim 1, wherein
a cleaning operation guide window to indicate an operation of removing the pollutant is displayed after the warning window is displayed and the cleaning operation indicated by the cleaning operation guide window is so arranged to vary according to the arrival time to the tolerance as being a time from the accumulated value is zero to the accumulated value exceeds the pollutant tolerance.

5. The exhaust gas analysis system described in claim 4, wherein
the shorter the arrival time to the tolerance is, the more intense cleaning operation is instructed.

6. The exhaust gas analysis system described in claim 1, wherein
the pollutant component meter is a THC meter that measures a concentration of THC in the exhaust gas flowing in the exhaust gas flow line.

7. The exhaust gas analysis system described in claim 1, wherein
the display control device displays a warning set window to set the pollutant tolerance and sets a numerical value input on the warning set window as the pollutant tolerance.

8. The exhaust gas analysis system described in claim 7, wherein
a plurality of exhaust gas flow lines are provided,
the measurement device is arranged on each of the exhaust gas flow lines respectively, and
the warning set window is so configured to be able to set the pollutant tolerance for each of the exhaust gas flow lines respectively.

9. The exhaust gas analysis system described in claim 1, wherein
the display control device displays a log display window showing log information that displays the warning window.

10. A program for an exhaust gas analysis system used for an exhaust gas analysis system having an exhaust gas flow line where an exhaust gas flows and a measurement device that is arranged in the exhaust gas flow line and that contains a pollutant component meter to measure a pollutant component as being a cause of the pollutant in the exhaust gas flow line, wherein
producing a warning display function that compares an accumulated value, that is obtained by accumulating measurement signal values from the pollutant component meter at predetermined sampling intervals and is only reset to zero when a purge is conducted, with a predetermined pollutant tolerance at a time of measuring the exhaust gas and that displays on a display a warning window that recommends a purge be conducted in response to the accumulated value exceeding the predetermined pollutant tolerance.

* * * * *